(12) United States Patent
Stuke et al.

(10) Patent No.: US 8,416,406 B2
(45) Date of Patent: Apr. 9, 2013

(54) SENSING DEVICE AND METHOD PRODUCING A RAMAN SIGNAL

(75) Inventors: Michael Josef Stuke, Palo Alto, CA (US); Shih-Yuan Wang, Palo Alto, CA (US); Zhiyong Li, Redwood City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 299 days.

(21) Appl. No.: 12/914,655

(22) Filed: Oct. 28, 2010

(65) Prior Publication Data
US 2012/0105840 A1 May 3, 2012

(51) Int. Cl.
*G01J 3/44* (2006.01)
(52) U.S. Cl. .................................. 356/301
(58) Field of Classification Search .......... 356/301, 356/72–73; 977/954
See application file for complete search history.

(56) References Cited

U.S. PATENT DOCUMENTS

| | | | |
|---|---|---|---|
| 7,713,849 B2 * | 5/2010 | Habib et al. | 438/479 |
| 2006/0057631 A1 | 3/2006 | Zou et al. | |
| 2009/0201496 A1 | 8/2009 | Lee et al. | |

FOREIGN PATENT DOCUMENTS

| | | |
|---|---|---|
| WO | WO2008/139419 | 11/2008 |
| WO | WO2010/055959 | 5/2010 |

OTHER PUBLICATIONS

Jiang, S., "Surface Enhanced Raman Scattering Spectroscopy," Term Paper for Physics 598 OS, http://www.ijvs.com/volume4/edition2/index.html.
von Maltzahn, et al., "SERS-Coded Gold Nanorods as Multifunctional Platform for Densely Multiplexed Near-Infrared Imaging & Photothern Heating," Adv Mat. 2009, 21, 3175-3180.
Liao, Q., et al., "Gold Nanorod Arrays with Good Reproducibility for High-Perform Surface-Enhanced Raman Scattering," Langmuir 2009, 25(8), 4708-4714.

\* cited by examiner

*Primary Examiner* — Tarifur Chowdhury
*Assistant Examiner* — Abdullahi Nur

(57) ABSTRACT

A sensing device that produces a Raman signal includes micro-rods or nano-rods arranged on a substrate in a two-dimensional (2D) array, each of the rods having a length in a single row being substantially the same, with the rod length of each row being different from the rod length of each other row. Each row of rods has a respective resonant vibration frequency that varies from row to row. A source of vibration energy, operatively connected to the substrate, excites vibration in each of the rods such that a responding row resonates when an exciting frequency approaches the resonant vibration frequency of the responding row. A method includes exposing the 2D array to a light source and analyzing Raman scattering at each rod of the 2D array to render a Raman map.

20 Claims, 3 Drawing Sheets

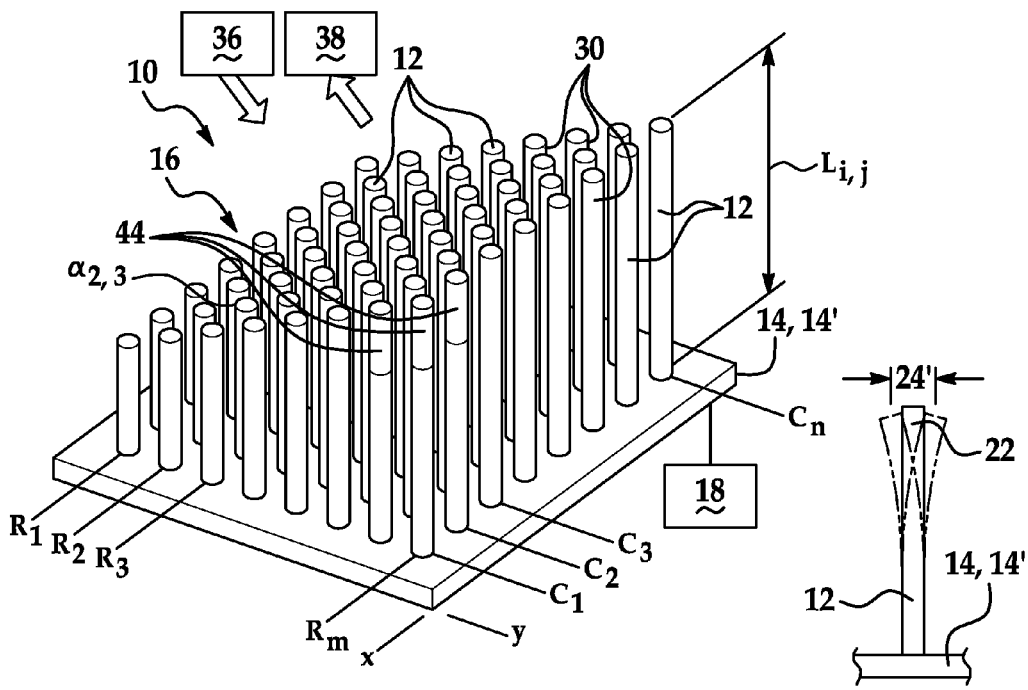
FIG. 1  FIG. 2
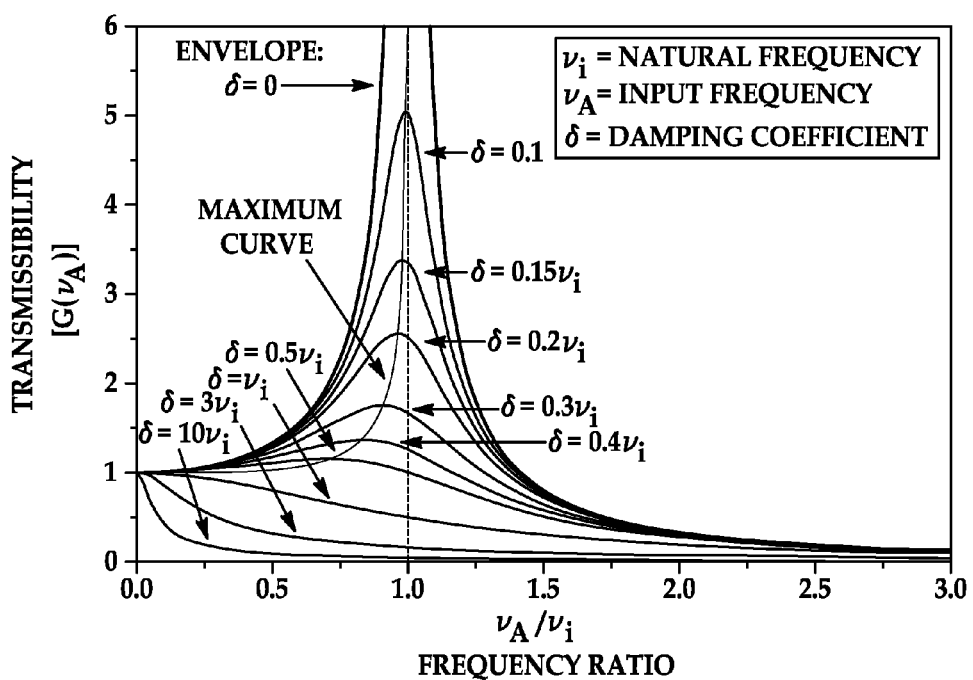
FIG. 3

SENSING DEVICE AND METHOD PRODUCING A RAMAN SIGNAL

STATEMENT REGARDING FEDERALLY SPONSORED RESEARCH OR DEVELOPMENT

This invention was made in the course of research partially supported by grants from the Defense Advanced Research Projects Agency (DARPA), Contract No. HR0011-09-3-0002. The U.S. government has certain rights in the invention.

BACKGROUND

The present disclosure relates generally to sensing devices that produce a Raman signal.

Raman spectroscopy is used to study the transitions between molecular energy states when photons interact with molecules, which results in the energy of the scattered photons being shifted. The Raman scattering of a molecule can be seen as two processes. The molecule, which is at a certain energy state, is first excited into another (either virtual or real) energy state by the incident photons, which is ordinarily in the optical frequency domain. The excited molecule then radiates as a dipole source under the influence of the environment in which it sits at a frequency that may be relatively low (i.e., Stokes scattering), or that may be relatively high (i.e., anti-Stokes scattering) compared to the excitation photons. The Raman spectrum of different molecules or matters has characteristic peaks that can be used to identify the species. As such, Raman spectroscopy is a useful technique for a variety of chemical or biological sensing applications. However, the intrinsic Raman scattering process may be inefficient in some instances, and rough metal surfaces, various types of nano-antennae, as well as waveguiding structures have been used to enhance the Raman scattering processes (i.e., the excitation and/or radiation process described above). This field is generally known as surface enhanced Raman spectroscopy (SERS).

BRIEF DESCRIPTION OF THE DRAWINGS

Features and advantages of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 1 is a semi-schematic perspective view of an example of the sensing device of the present disclosure;

FIG. 2 is an enlarged, partially cutaway side view of an example of a single micro- or nano-rod showing a deflection envelope;

FIG. 3 depicts a resonance transmissibility diagram of an example of the sensing device of the present disclosure;

DETAILED DESCRIPTION

Figure 8:
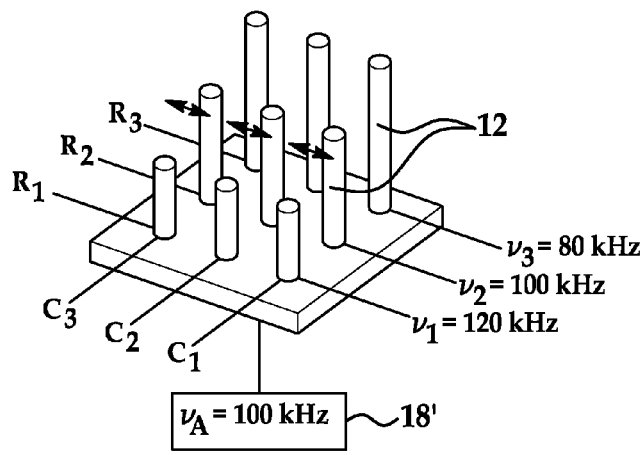
FIG. 8 is a semi-schematic perspective view of an example of the sensing device of the present disclosure depicting a responding row in resonance.

Sensitivity and selectivity for detection of small amounts of molecules are often very difficult, if not impossible or impractical, due to the lack of sufficiently suitable identification patterns. Detector chips based on structured substrate surfaces on the nanoscale have been proposed for surface enhanced Raman spectroscopy (SERS) and other detection techniques including laser-induced fluorescence (LIF). However, many of these devices lack selectivity due to the lack of sufficient selectivity of the Raman spectra. Other approaches include mass spectrometry using laser-induced species removal and mass identification; however, this approach is bulky, affects the surface and is not sufficiently spectrally selective.

The present inventors have unexpectedly and fortuitously discovered a highly selective and sensitive detector/sensor device that produces a Raman signal. Examples of the present device and method as described herein are capable of detecting by Raman spectroscopy or by surface enhanced Raman spectroscopy (SERS) ultrasmall amounts, e.g., down to the single molecule level. This allows surface selective detection, and, depending on the location on the surface, the identification of the adsorbed/trapped species. Sensitivity and selectivity of a human nose can be achieved and often exceeded.

In general, examples of the present disclosure include a substrate surface chip, on which a two-dimensional (2D) array of rods on the micro- and nano-scale are formed using a range of possible techniques. These rods have resonant vibration frequencies related to their shear modulus, mass density, dimension (cross sectional area and length) and the material/material combinations from which the rods are formed. The array of rods is prepared in such a way that their vibration frequency is changing in one dimension, for example in the x-direction (or in the y-direction). The 2D array of rods may be used for many applications, e.g., as an indirect vibration sensor. Further, when the 2D array includes labeling for selective molecular adsorption (as in some examples of the present disclosure described herein), the labeling changes in the same direction as the vibration frequency, or in another dimension, for example in the y-direction (or in the x-direction). In this way, ultrasmall amounts of small and complex molecules may be detected and identified with high selectivity and sensitivity using the position on the surface chip.

Examples of the present disclosure allow fabrication of a highly sensitive and selective, reliable, compact and low-cost detection system that can operate at ambient pressure conditions without damaging the substrate surface.

Referring now to FIG. 1, an example of a sensing device for producing a Raman signal according to the present disclosure is depicted generally at 10. A plurality of micro- or nano-rods 12 is arranged in rows $R_i$ (i=1-m) and columns $C_j$ (j=1-n) on a substrate 14 in a two-dimensional (2D) array 16. As used herein, each micro- or nano-rod 12 is an element of 2D array 16 with a position in the 2D array 16 designated by $\alpha_{i,j}$. For example, $\alpha_{2,3}$ designates a micro- or nano-rod 12 in row $R_2$ and column $C_3$. The indexing scheme using i and j to designate, respectively, row and column positions in the array is used throughout the present disclosure. Although an 8×8 array is shown in FIG. 1, it is to be understood that the quantity of rows and columns m,n respectively may range from as few as 2,2 to three or more orders of magnitude larger (i.e., tens of thousands or more).

In the examples herein, each of the micro- or nano-rods 12 has a length $L_{i,j}$ extending outwardly from the substrate 14. The length $L_{i,j}$ of each micro- or nano-rod 12 in a single row $R_i$ is substantially the same, and may be designated as $L_i$. The micro- or nano-rod length $L_i$ of each row $R_i$ is different from the micro- or nano-rod length $L_{(not\,i)}$ of each other row $R_{(not\,i)}$, and each row $R_i$ of micro- or nano-rods 12 has a respective resonant vibration frequency $v_i$ that varies from row $R_i$ to row $R_{(not\,i)}$.

Although the micro- or nano-rods 12 are shown in the figures herein as rods having a disk-shaped cross section, it is to be understood that the rods 12 may have any desired cross section, shape or combination of shapes, as long as the rods 12 have an aspect ratio (smallest base dimension to length) sufficient to allow the rods 12 to vibrate/resonate, producing displacement and substantial contact of the tips of the rods 12 as disclosed herein. For example, the rods 12 may have a rectangular cross section. In a further example, the rods 12 may be cone shaped or pyramidal shaped, terminating at a point region distal to the substrate 14 surface.

It is to be understood that the micro- or nano-rods 12 may be formed by any suitable method. Some examples of suitable methods include: self organization; creating grooves in substrate 14 surface and operatively disposing an end of the rods 12 therein; growing the rods 12 from the substrate 14 using e.g., laser induced growth using a precursor target; growing the rods 12 using atomic layer epitaxy (ALE) (which allows length control down to Angstrom precision); nano-imprint lithography; metal organic chemical vapor deposition (MOCVD); the vapor-liquid-solid (VLS) method; or the like; or combinations thereof.

Further examples of suitable SERS substrates and/or methods for making these substrates are described in the following International or U.S. patent application Serial Numbers: PCT/US10/31790, filed Apr. 20, 2010 and entitled "Multi-Pillar Structure for Molecular Analysis"; PCT/US10/31809, filed Apr. 20, 2010 and entitled "A Self-Arranging, Luminescence Enhancement Device for Surface-Enhanced Luminescence"; and Ser. No. 12/771,440, filed Apr. 30, 2010 and entitled "Surface-enhanced Raman Spectroscopy Device and a Mold for Creating and a Method for Making the Same"; all of which are incorporated herein by reference.

An example of a vapor-liquid-solid (VLS) method for forming the micro- or nano-rods 12 on the substrate 14 includes establishing at least two different catalyzing micro- or nano-particles on a crystalline substrate 14. The catalyzing particles enable substantially simultaneous growth of a micro- or nano-rod 12 from each of at least two different catalyzing particles. At least one of the rods 12 has a length different from that of at least one other of the rods 12. It is to be understood that the substrate 14 may have a plurality of catalyzing particles established thereon or therein (e.g., established on, and substantially raised from the surface of the substrate 14; or established on, or in the substrate 14 surface such that they are substantially level with the surface; or established in depressions formed in the substrate 14 surface).

It is to be understood that the catalyzing particles may be established on, substantially level with, or in the substrate surface via a variety of techniques (e.g., imprinting the particles via an imprint device (e.g., a mold or a stamp); using a sacrificial layer (e.g. a masking layer, a resist layer, and/or the like) and forming a pattern in the sacrificial layer. Imprint lithography may also be used. Still other methods of establishing the catalyzing particles include agglomeration of a thin catalyst material during heat treatment, strain-induced self-assembly, or deposition of pre-formed catalyst particles.

The rods 12 may be substantially simultaneously grown from the catalyzing particles. It is to be understood that supplying heat and precursor gases of the material(s) forming the rods 12 may be used to initiate growth of the rods 12 at an area between the substrate 14 and the particles. Alternately, growth may be initiated by supplying atoms of the materials that form the rods 12 (e.g., by laser ablation).

It is believed that the size and/or shape of the catalyzing particles determines, at least in part, the size (e.g., the length in the z-direction and/or diameter) of the resulting rod 12. As such, the growth rate of the rods 12 may be selectively controlled by selecting or forming desirable catalyzing particles.

Figure 1A:
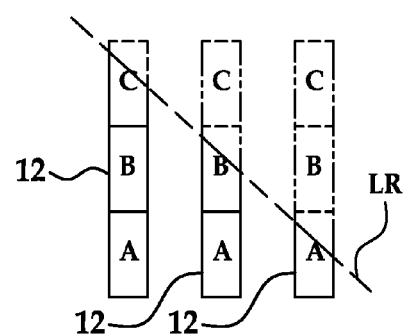
FIG. 1A is a semi-schematic representation of an example of a method of forming micro- or nano-rods according to an example of the present disclosure.

Referring now to FIG. 1A, an example of forming micro- or nano-rods 12 includes forming rods 12 from a heterostructure of material A, material B and material C. If desired, the rods 12 could remain as formed (as shown in phantom line) with material C distal to the substrate 14 surface (not shown in FIG. 1A). The rods 12 may also be (angularly as shown, if desired) cut, etched or otherwise selectively shortened (e.g., such as at cut line LR) such that two or more materials respectively form the rod 12 surfaces distal to the substrate 14 surface. In the example shown in FIG. 1A, from left to right, this distal rod 12 material (shown in solid line) is material C, material B and material A.

Referring again to FIG. 1, a source 18 of vibration energy is operatively connected to the substrate 14 for exciting vibration in each of the micro- or nano-rods 12 in the 2D array 16 such that a responding row $R_i$ resonates when an exciting frequency $v_A$ approaches the resonant vibration frequency $v_i$ of the responding row $R_i$.

In examples of the present disclosure, each of the micro- or nano-rods 12 includes a label 30 to provide a distinct Raman signal (either itself and/or after being bound to an analyte of interest). The label 30 of each micro- or nano-rod 12 in a single column $C_j$ may be substantially the same, with the micro- or nano-rod label 30 of each column $C_j$ being different from the micro- or nano-rod label 30 of each other column $C_{(not\,j)}$ such that each column $C_j$ is for producing a different distinct Raman signal. The variation in the length $L_{i,j}$ of the micro- or nano-rods 12 in a column $C_j$ causes the distinct Raman signal for the commonly labeled micro- or nano-rods 12 in the column $C_j$ to be emitted at different frequencies depending on the resonant vibration frequency $v_i$ of the micro- or nano-rods 12 in the column $C_j$.

In other examples, the label 30 of each micro- or nano-rod 12 in a single row $R_i$ may be substantially the same, with the micro- or nano-rod label 30 of each row $R_i$ being different from the micro- or nano-rod label 30 of each other row $R_{(not\,i)}$ such that each row $R_i$ is for producing a different Raman signal.

One or more photodetector(s) 38 may be used to detect the Raman signal(s) for analysis. It is to be understood that the photodetector(s) 38 may be any device that can detect light/photons, either alone or in combination with a suitable high transmission filter or another wavelength selective device. In an example, the photodetector 38 is chosen from a photodiode, a phototransistor, an avalanche photodiode, a calibrator, or any other suitable photodetector.

In yet other examples, the label 30 of each micro- or nano-rod 12 in the 2D array 16 may be unique, and produce a Raman signal distinct from the Raman signal produced by the label 30 of each and every other micro- or nano-rod 12.

It is to be understood that a particular type of label 30 may be associated with a group of micro- or nano-rods 12; for example associated with row $R_i$ or with column $C_j$. Alternatively, the type of label 30 may be independent of groups or patterns of micro- or nano-rods 12 in the 2D array 16.

Further, in some examples of the present disclosure, any suitable label 30 may be used that is a Raman active material. In other examples as disclosed herein, the label 30 will selectively bind an analyte of interest, and the bound molecule will emit a Raman signal.

The rods 12 themselves will generally not give any Raman signal. The Raman signal comes from molecules (e.g., a Raman dye as a label 30 on the rod 12 surface, or analyte molecules (e.g., analyte, species of interest, predetermined species) selectively bound to the label 30 (e.g., a binding agent in this example) attached to the rod 12 surface). For analyte molecule detection, the bound analyte itself would emit the Raman signal. In a further example, a Raman dye may be chemically attached to the bound analyte molecule. In yet a further example, a Raman dye may be co-attached to the rod 12 surface as a result of the label 30/binding agent-analyte binding.

Examples of Raman dyes/labels 30 include organic molecules that have large Raman cross-sections and can adhere well on metal surfaces. As such, examples of suitable Raman dyes/labels 30 should have at least a binding group, such as a thiol or pyridyl or amine group that allows the assembly of the dye/label 30 on the metal surfaces. In order to have a large Raman cross-section, typically at least an aromatic ring with high conjugation is included. Some examples of Raman active materials include BPE (bispyridinal ethylene), mercaptobenzene, mercaptophenol, R6G (rodamine 6G), pyridine, pyridine derivatives, or the like, or combinations thereof.

It is to be understood that the label 30 chemically functionalizes the surface of the rods 12. This functionalization may be accomplished by any suitable method. Some examples of suitable methods include: selective inkjet deposition of the label 30 on the surface/tip region 44 of the rods 12; selectively addressing each row/column of rods 12 with electrodes to initiate desired redox reactions; photolithography; or the like.

In examples of sensing device 10 of the present disclosure, the micro- or nano-rods 12 are coated with, or formed from a Raman signal enhancing material (a rod 12 is shown in FIG. 1 having its tip region 44 coated with the Raman signal enhancing material). The label 30 is disposed on top of the Raman signal enhancing material. It is to be understood that any material which may be structured in the lateral or vertical direction may be suitable as a Raman signal enhancing material. For example, nanoscale carbon, such as graphene, may be used due to its very high electron mobility. Further examples of Raman signal enhancing materials include aluminum, gold, silver, copper, alloys thereof, and combinations thereof.

In examples where the rods 12 are coated with the Raman signal enhancing material, it is to be understood that at least a portion 44 of the micro- or nano-rod 12 (if not the whole rod 12) may be coated with the Raman signal enhancing material. For example, 25 percent of the length $L_{i,j}$ of a micro- or nano-rod 12 at an end portion/tip region 44 distal to the substrate 14 may be coated by the Raman signal enhancing material. In another example, 10 percent or less of the length $L_{i,j}$ of a micro- or nano-rod 12 at an end portion/tip region 44 distal to the substrate 14 may be coated by the Raman signal enhancing material. In an example, enough of the rod 12 tip region 44 is coated such that when adjacent rod ends 44 approach each other, the approaching ends 44 are both coated with the Raman signal enhancing material. It is to be understood that if one or both rods 12/tip regions 44 are coated with/formed from the Raman signal enhancing material, then the Raman signal is strongly enhanced by the signal enhancing material in combination with the small distances between the rod tip regions 44 and/or between the rods 12 and bound molecules/analytes of interest.

It is to be understood that the micro- or nano-rods 12 may be any metal or metal-coated plasmonic micro- or nano-rods (i.e., having at least one dimension ranging from about 1 nm to about 3 microns; or from about 10 nm to about 100 nm; or less than 10 nm) that amplify the Raman scattering when exposed to light (e.g., laser illumination). The metal or metal-coating is a Raman signal enhancing material, or a material that is capable of increasing the number of Raman scattered photons when the rod 12 and/or analyte of interest are subjected to electromagnetic radiation.

In an example, the rod 12 diameter size ranges from about 20 nm to about 300 nm. The aspect ratio (smallest base dimension to length) of the rods 12 may be any suitable ratio as desired. In some examples, the aspect ratio of the rods 12 may be 1 to 1,000,000 and above (or any aspect ratio therebetween). In another example, the aspect ratio may be 10 to 1000.

It is to be understood that since Raman scattering is isotropic, Raman photons may be collected in a reflective mode or in a transmission mode depending upon the transparency of the substrate 14. In some instances, the collection efficiency may be increased by placing an antenna on a reflective mirror substrate.

Further, it is to be understood that any suitable substrate 14 may be chosen. Examples of suitable substrates 14 include piezoelectric materials, metal materials, semiconductor materials, polymeric materials, and combinations thereof. Examples of suitable piezoelectric materials include $BaTiO_3$, $PbZrTiO_3$, polyvinylidene difluoride (PVDF), and/or the like, and/or combinations thereof. Examples of suitable metal materials include aluminum, platinum, chromium, and/or other like metals, and/or alloys thereof (e.g., silicides), and/or combinations thereof. Examples of suitable semiconductor materials include group IV materials (e.g., Si, Ge, etc.), group III-V materials (e.g., GaAs, InP, etc.), group II-VI materials (e.g., ZnSe, ZnS, etc.), transition metal oxides (e.g., $TiO_2$, etc.), and/or the like, and/or combinations thereof. Further examples of suitable substrate materials include glass, spin-on glass, quartz, nitrides, alumina, sapphire, polymers (e.g., polycarbonate, polyimide, acrylic, polyester sheets/films (e.g., MYLAR, commercially available from DuPont Teijin, Hopewell, Va.), etc.), combinations thereof, and/or layers thereof.

In an example having a substrate 14 that is piezoelectric, the source 18 of vibration energy may be an electrical signal that drives the piezoelectric substrate 14', thereby causing the piezoelectric substrate 14' to vibrate at a predetermined frequency. In other examples, the substrate 14 may be mechanically connected to a vibrating structure, for example by attachment to, or contact with a vibrating mass. In still other examples, the substrate 14 may be caused to vibrate without direct contact to the source 18 of vibration energy, for example by acoustic energy transfer, or by the impingement of pulsed laser energy on the substrate 14. It is to be understood that all of the above are examples of a source 18 of vibration energy operatively connected to the substrate 14 for exciting vibration.

The source 18 of vibration energy may be an impulse source for exciting broadband vibration in the substrate. In other examples of the present disclosure, the source 18 of vibration energy may be a frequency sweeping source for exciting a range of vibration frequencies in a sweeping narrow band in the substrate 14. In still further other examples, the source 18 of vibration energy may be a fixed frequency source that dwells on a particular narrow band for an extended period of time. In examples of the present disclosure applied as a vibration or sound sensor, the source 18 of vibration energy may be any source of vibration or sound energy, for example: a spoken voice, a vibrating mass, or a musical instrument.

When excited by a source 18 of vibration energy, the micro- or nano-rods 12 will experience transverse vibration. It is to be understood that vibration of the substrate 14 causes transverse vibration of the plurality of micro- or nano-rods 12. FIG. 2 shows in phantom line an example of first mode transverse vibration of a micro- or nano-rod 12. It is to be further understood that the vibration of substrate 14 is not necessarily in the same direction as the transverse vibration of the micro- or nano-rods 12.

Figure 4:
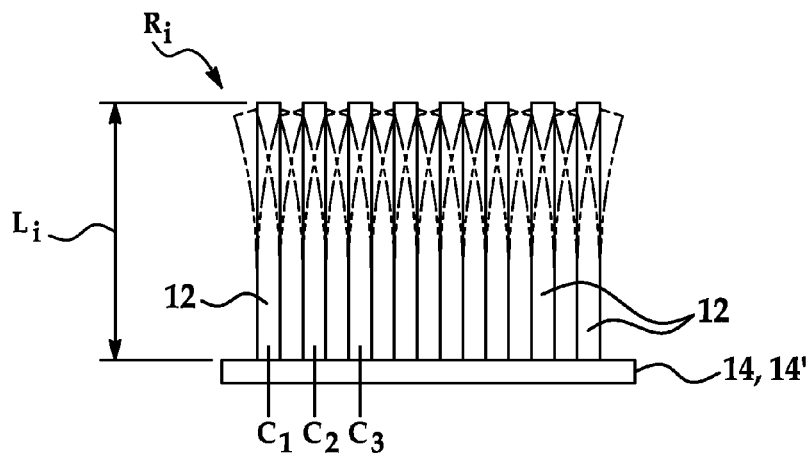
FIG. 4 is a side view of the example of the sensing device depicted in FIG. 1, showing displacement envelopes for resonating micro- or nano-rods.

Referring now to FIG. 3, as source vibration frequency $v_A$ approaches the resonant frequency $v_i$, a transmissibility of the vibration from the source to the micro- or nano-rods 12 will grow to greater than 1. It is to be understood that, as depicted in FIG. 3, "transmissibility" is defined as a ratio of response vibration amplitude (i.e., displacement of the micro- or nano-rods 12) to input vibration amplitude (i.e., displacement of the substrate 14). In examples of the sensing device 10 of the present disclosure, vibration is transmitted through the substrate 14 to the micro- or nano-rods 12. As the substrate 14 is excited at a frequency $v_A$ close to the resonant frequency $v_i$ of a micro- or nano-rod 12, the micro- or nano-rod will resonate in at least the first mode (as shown in FIG. 2), and the free end of the micro- or nano-rod 12 may periodically substantially contact an adjacent micro- or nano-rod 12 (as shown in FIG. 4). It is to be understood that in an example, the adjacent micro- or nano-rod 12 may be in the same row as the resonating micro- or nano-rod 12, while in another example, the contact may be with a micro- or nano-rod 12 in an adjacent row. In yet another example, the micro- or nano-rod 12 may, at distinct instances, contact adjacent micro- or nano-rods 12 in the same row and in an adjacent row. In an example, at the point of contact, the rods 12 are coated with (or formed from) the Raman signal enhancing material and have the label 30 thereon.

Actual contact between the micro- or nano-rods 12 damps vibration and prevents resonance from causing the unlimited absorption of energy shown as a singularity for an undamped system (i.e., for small delta) where the frequency ratio $v_A/v_i$ is exactly 1 in FIG. 3.

As used herein, "substantially contact" means one micro- or nano-rod 12 actually contacts an adjacent micro- or nano-rod 12 (or are about 0.1-0.9 nm apart, e.g., when the rod 12 surfaces are rough); or comes within about 1-6 nm of actually touching; or comes within about 5-1000 nm of actually touching. It is to be understood that when a micro- or nano-rod 12 with a Raman active surface substantially contacts another micro- or nano-rod 12 with a Raman active surface, a Raman signal will be amplified by as many as eight or more orders of magnitude compared to a Raman signal emitted from the Raman active surfaces when they are farther apart.

It is to be understood that the periodic amplification of the Raman signal that results from periodic substantial contact between the micro- or nano-rods 12 is manifested as a Raman signal "blinking" or "flashing" at the frequency of "substantial contact" of the micro- or nano-rods 12 having the Raman signal enhancing material and a label 30/bound analyte thereon that produces a Raman signal. By using frequency tracking, or phase-lock detection to lock in on the periodic "blinking" Raman signal, the Raman signal can be separated from noise (e.g., background fluorescence) that would otherwise interfere with accurate detection and analysis of the Raman signal. As such, examples of the present disclosure may therefore amplify the Raman signal by as much as 12 orders of magnitude, while making the Raman signal distinguishable from noise by emitting the Raman signal at periodic intervals that enable phase-lock detection of the Raman signal.

Without being bound to any theory, it is believed that the largest Raman enhancement happens when the rod tips 22/tip regions 44 substantially contact each other. The enhancement (i.e., the Raman signal from the molecules on the rod 12 surface) decays almost exponentially with the separation distance between rod tips 22. Due to this nonlinear dependence, the vibration of the rods 12 will provide the time variance of the Raman signal.

FIG. 4 depicts a row $R_i$ of micro- or nano-rods 12. Each of the micro- or nano-rods 12 in the row $R_i$ is substantially the same length $L_i$. As used herein, substantially the same length means exactly the same length, or having a length ranging between about 1 percent greater and 1 percent less; or in another example +/−5% (for a lower performance device); or in yet another example, +/−0.5% (for a higher performance device). It is to be understood that although FIG. 4 depicts a quantity of 8 micro- or nano-rods 12 in the row $R_i$, as few as two and as many as tens of thousands or more micro- or nano-rods 12 in the row $R_i$ are contemplated as being within the purview of the present disclosure.

Figure 5:
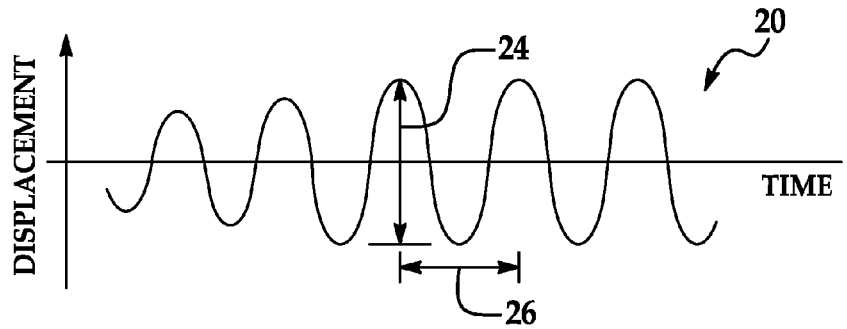
FIG. 5 depicts a displacement waveform for a micro- or nano-rod depicted in FIG. 4 as the micro- or nano-rod approaches resonance.

FIG. 5 is a graphical depiction of a waveform 20 describing the motion of a tip 22 (depicted in FIG. 2) of a micro- or nano-rod 12 as the micro- or nano-rod 12 approaches and sustains resonance. An amplitude 24 of the waveform 22 corresponds to an amplitude 24' of the micro- or nano-rod 12 depicted in FIG. 2. A period 26 of the waveform 22 is shown at resonance.

Figure 6:
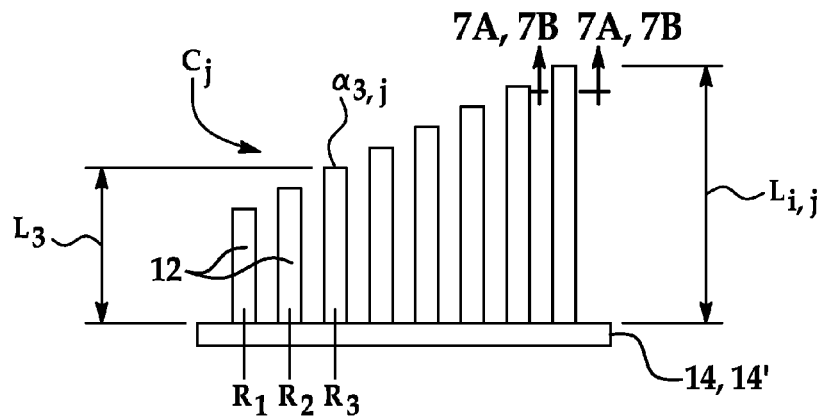
FIG. 6 is a front view of the example of the sensing device depicted in FIG. 1.

FIG. 6 depicts a column $C_j$ of micro- or nano-rods 12. Using the indexing scheme provided above, each of the micro- or nano-rods 12 in the column $C_j$ is designated $\alpha_{i,j}$. The length $L_{i,j}$ of each micro- or nano-rod 12 at $\alpha_{i,j}$ is substantially different from the length $L_{(not\ i,j)}$ of each other micro- or nano-rod 12 at $\alpha_{(not\ i,j)}$. As used herein, a substantially different length means longer or shorter by about 5 percent of the compared length. It is to be understood that although FIG. 6 depicts a quantity of 8 micro- or nano-rods 12 in the column $C_j$, as few as two and as many as tens of thousands or more micro- or nano-rods 12 in the column $C_j$ are contemplated as being within the purview of the present disclosure. It is to be further understood that although FIG. 1 and FIG. 6 depict length $L_{i,j}$ increasing with increasing i, examples of the sensing device 10 of the present disclosure may have no particular order of length $L_{i,j}$, provided that every length $L_{i,j}$ in a row $R_i$ is substantially the same (as in the description of FIG. 4 above).

The resonant vibration frequency $v_i$ of micro- or nano-rods 12 in each row $R_i$ is related to shear modulus, mass density, cross sectional area, length, and a material forming or coating the micro- or nano-rods 12 in the respective row $R_i$. In an example where the micro- or nano-rods 12 are cantilevers of length $L_i$ with uniform, disk shaped cross-sections over the length $L_i$, the resonant frequency $v_i$ of transverse vibration of a cantilever micro- or nano-rod 12 is:

$$v_i = \frac{0.254}{L_i^2} \sqrt{\frac{AG}{\rho}} \qquad \text{Eq. (1)}$$

$v_i$ natural frequency (MHz)
$L_i$ length of cantilever (cm)
A cross-sectional area of cantilever (cm$^2$)
G shear modulus (GPa)
$\rho$ mass density (g/cm$^3$)
i designates a row in an array
The shear modulus G for various materials is listed in Table 1:

TABLE 1

| Material | G (GPa) |
|---|---|
| Diamond | 47.8 |
| Steel | 79.3 |
| Copper | 44.7 |
| Titanium | 41.4 |
| Glass | 26.2 |
| Aluminum | 25.5 |
| Polyethylene | 0.117 |
| Rubber | 0.0006 |

Figure 7A:
FIGS. 7A and 7B each depict an example of a cross section of the micro- or nano-rod taken along line 7A-7A, 7B-7B in FIG. 6.
Figure 7B:
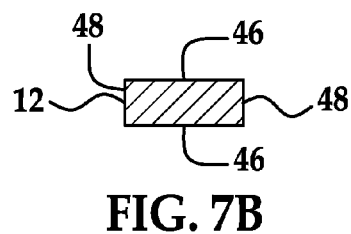

FIGS. 7A and 7B depict cross sections of examples of the micro- or nano-rods 12 taken along lines 7A-7A, 7B-7B in FIG. 6. FIG. 7A is a disk-shaped cross section which will correspond to isotropic bending stiffness in the micro- or nano-rods 12. Eq. (1) assumes that the cross-section used to determine the cross sectional area A is disk-shaped. It is to be understood that other examples of the present disclosure may have micro- or nano-rods 12 with anisotropic bending stiffness. For example, micro- or nano-rods 12 with a rectangular cross-section as depicted in FIG. 7B will have a greater bending stiffness corresponding to longer sides 46 of the rectangle, and a lower bending stiffness corresponding to shorter sides 48 of the rectangle. Because of the different bending stiffnesses, a micro- or nano-rod 12 with anisotropic bending stiffness may resonate at different frequencies in different directions. It is to be understood that Eq. (1) may not provide an accurate estimate of the resonant frequencies of micro- or nano-rods 12 having anisotropic bending stiffness. It is to be further understood that the frequencies of micro- or nano-rods 12 with anisotropic bending stiffness will, similarly to the examples with disk-shaped cross-sections, be a function of the dimensional and material properties of the micro- or nano-rods 12, with a sensitivity to length $L_{i,j}$ of the micro- or nano-rods 12.

By aligning the anisotropic micro- or nano-rods 12 such that the lowest bending stiffness leads to bending in a plane parallel to a row $R_i$ of matched-frequency micro- or nano-rods, unintended contact with micro- or nano-rods in adjacent rows may be reduced. In examples of the present disclosure, each of the micro- or nano-rods 12 may have a cross-sectional shape for predisposing the micro- or nano-rods 12 to move in a predefined direction when the micro- or nano-rods 12 are resonating.

In some examples, a resonating micro- or nano-rod 12 may contact adjacent micro- or nano-rods 12 in the same row $R_i$; however, in other examples, the resonating micro- or nano-rods 12 may contact any other micro- or nano-rod 12.

A sensing method is disclosed herein. In examples of the disclosed method, vibration in each micro- or nano-rod 12 in the two dimensional (2D) array 16 of the plurality of micro- or nano-rods 12 arranged in rows $R_i$ (i=1–m) and columns $C_j$ (j=1–n) on substrate 14 is excited. Under such excitation, a responding row resonates when an exciting frequency approaches a resonant vibration frequency of the responding row. For example, FIG. 8 shows a responding row $R_2$ resonating when the exciting frequency $v_A$ approaches the resonant frequency $v_2$ of the responding row $R_2$. In the example shown, row $R_2$ resonates at 100 kHz, which equals the exciting frequency $v_A$.

In examples of the disclosed method, the 2D array 16 is then exposed to a light source 36 (shown in FIG. 1). It is to be understood that the light source 36 may be any monochromatic light source 36. An example of a monochromatic light source 36 is a laser emitting light with a wavelength between about 730 nm and about 740 nm. The monochromatic light source 36 may be of any wavelength that causes the label 30/bound analyte to emit a Raman signal without destroying a molecule to be detected. For example, some molecules could be destroyed by UV light. If such a UV-sensitive molecule was targeted by the sensing device 10, then UV light should be avoided as the monochromatic light source 36. In examples of the present disclosure, wavelengths of light from blue to near IR may be used, as desired and/or depending upon the application.

Raman scattering at each micro- or nano-rod 12 of the 2D array 16 is detected by photodetector(s) 38, and is analyzed to render a Raman map. It is to be understood that analyzing of the Raman scattering at each micro- or nano-rod 12 of the 2D array 16 may be performed serially or in parallel on groups of resonating micro- or nano-rods 12. Serial analysis of the Raman scattering may be well suited for examples of the present disclosure wherein the source 18 of vibration energy is a frequency sweeping source for exciting a range of vibration frequencies in a sweeping narrow band in the substrate 14. In other examples of the present disclosure, parallel processing may provide faster analysis. Parallel processing may be well suited to examples of the present disclosure wherein the source 18 of vibration energy is an impulse source for exciting broadband vibration in the substrate 14.

Figure 9:
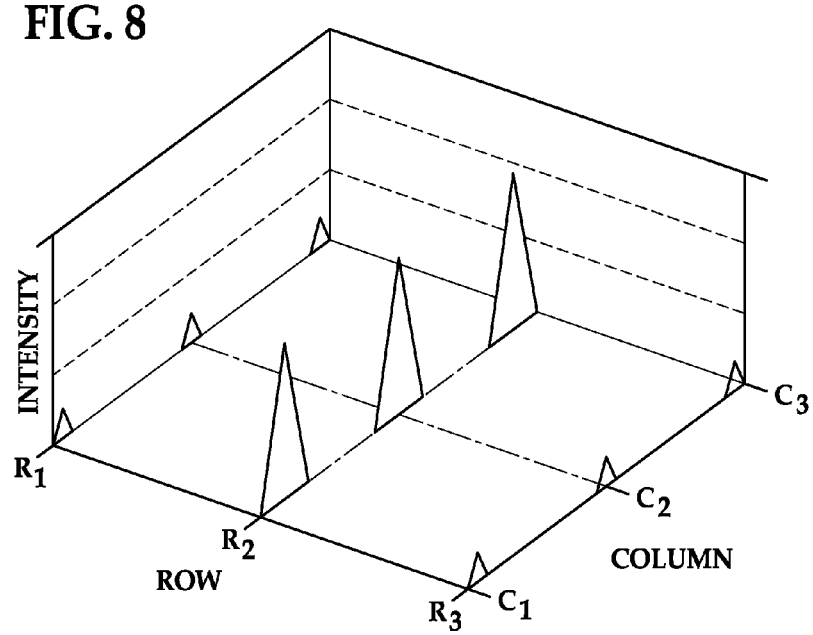
FIG. 9 is an example of a Raman map from the example depicted in FIG. 8.

From the Raman map, an exciting frequency spectrum of a source 18 of vibration energy that excites the vibration in each micro- or nano-rod 12 is deduced. For example, FIG. 9 is a Raman map that shows that row $R_2$ is resonating. If, for the purposes of the example, it is known that the micro- or nano-rods 12 in row $R_2$ resonate at 100 kHz, then it can be deduced that the source 18' of vibration energy (FIG. 8) is vibrating at 100 kHz. In examples of the present disclosure, the frequency may typically range from about 100 kHz to GHz, depending on the material and its dimensions (e.g., diamond has a higher frequency due to its high stiffness, whereas soft organic polymers have a lower frequency).

Examples of the disclosed method may further include determining a highest Raman signal on the Raman map. The highest Raman signal may be determined by selecting the highest peak on the Raman map, or by integrating the area under a band surrounding a peak and choosing the largest integrated area.

Figure 10:
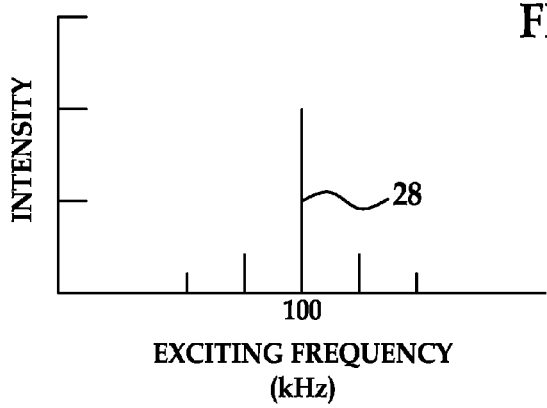
FIG. 10 is a Raman frequency spectrum for a single micro- or nano-rod from the example depicted in FIG. 8.

A dominant exciting frequency may be deduced from the exciting frequency spectrum. For example, FIG. 10 shows that the dominant exciting frequency 28 for the corresponding micro- or nano-rod 12 is 100 kHz.

It is to be understood that exciting frequency spectra may be generated continuously over a period of time. As such, the sensing device 10 according to examples of the present disclosure may be used as very sensitive remotely sensed microphones, hearing enhancement devices such as cochlear implants, and ultra-sensitive vibration detectors.

It is to be understood that the ranges provided herein include the stated range and any value or sub-range within the stated range. For example, an amount ranging from about 5 nm to about 1000 nm should be interpreted to include not only the explicitly recited amount limits of about 5 nm to about 1000 nm, but also to include individual amounts, such as 7 nm, 100 nm, 500 nm, etc., and sub-ranges, such as 10 nm to 50 nm, etc. Furthermore, when "about" is utilized to describe a value, this is meant to encompass minor variations (up to +/−10%) from the stated value.

While several examples have been described in detail, it will be apparent to those skilled in the art that the disclosed examples may be modified. Therefore, the foregoing description is to be considered non-limiting.

What is claimed is:

1. A sensing device for producing a Raman signal, comprising:
   a plurality of micro-rods or nano-rods arranged in rows and columns on a substrate in a two-dimensional (2D) array, each of the micro-rods or nano-rods having a length extending outwardly from the substrate, the length of each micro- or nano-rod in a single row being substantially the same, with the micro- or nano-rod length of each row being different from the micro- or nano-rod length of each other row, and each row of micro-rods or nano-rods having a respective resonant vibration frequency that varies from row to row;
   a source of vibration energy, operatively connected to the substrate, for exciting vibration in each of the micro-rods or nano-rods in the 2D array such that a responding row is to resonate when an exciting frequency approaches the resonant vibration frequency of the responding row; and
   a free end of each of the micro-rods or nano-rods to substantially contact an adjacent micro-rod or nano-rod when vibration is excited.

2. The sensing device as defined in claim 1 wherein the substrate is chosen from a piezoelectric material, a metal material, a semiconductor material, polymeric membranes, and combinations thereof.

3. The sensing device as defined in claim 1 wherein each of the micro-rods or nano-rods includes a label for producing a distinct Raman signal.

4. The sensing device as defined in claim 3 wherein the label comprises a Raman dye.

5. The sensing device as defined in claim 3 wherein the label comprises a molecule or compound for selectively binding to an analyte of interest.

6. The sensing device as defined in claim 1 wherein each of the micro-rods or nano-rods includes a label, the label of each micro- or nano-rod in a single column being substantially the same, with the micro- or nano-rod label of each column being different from the micro- or nano-rod label of each other column, such that each column is for producing a different distinct Raman signal.

7. The sensing device as defined in claim 1 wherein the micro-rods or nano-rods are coated with or formed from a Raman signal enhancing material.

8. The sensing device as defined in claim 7 wherein the Raman signal enhancing material is chosen from aluminum, gold, silver, copper, alloys thereof, graphene, and combinations thereof.

9. The sensing device as defined in claim 1 wherein each of the micro-rods or nano-rods has an anisotropic bending stiffness.

10. A sensing method, comprising:
    exciting vibration in each micro- or nano-rod in a two dimensional (2D) array of a plurality of micro-rods or nano-rods arranged in rows and columns on a substrate such that a responding row resonates when an exciting frequency approaches a resonant vibration frequency of the responding row and a free end of each of the micro-rods or nano-rods in the 2D array substantially contacts an adjacent micro-rod or nano-rod, each of the micro-rods or nano-rods having a length extending outwardly from the substrate, the length of each micro- or nano-rod in a single row being substantially the same, with the micro- or nano-rod length of each row being different from the micro- or nano-rod length of each other row, and each row of micro-rods or nano-rods having a respective resonant vibration frequency that varies from row to row;
    then exposing the 2D array to a light source; and
    analyzing Raman scattering at each micro- or nano-rod of the 2D array to render a Raman map.

11. The sensing method as defined in claim 10, further comprising deducing, from the Raman map, an exciting frequency spectrum of a source of vibration energy that excites the vibration in each micro- or nano-rod.

12. The sensing method as defined in claim 11, further comprising:
    determining a highest Raman signal on the Raman map; and
    deducing a dominant exciting frequency, based at least in part on the highest Raman signal, from the exciting frequency spectrum.

13. The sensing method as defined in claim 11, further comprising generating exciting frequency spectra continuously over a period of time.

14. The sensing method as defined in claim 10 wherein a micro- or nano-rod in the responding row substantially contacts an adjacent micro- or nano-rod when the micro-rods or nano-rods are resonating.

15. The sensing method as defined in claim 10 wherein each of the micro-rods or nano-rods has a cross-sectional shape for predisposing the micro-rods or nano-rods to move in a predefined direction when the micro-rods or nano-rods are resonating.

16. The sensing method as defined in claim 10 wherein the source of vibration energy is an impulse source for exciting broadband vibration in the substrate, and wherein the analyzing of the Raman scattering at each micro- or nano-rod of the 2D array is performed in parallel on groups of micro-rods or nano-rods.

17. The sensing method as defined in claim 10 wherein the source of vibration energy is a frequency sweeping source for exciting a range of vibration frequencies in a sweeping narrow band in the substrate, and wherein the analyzing of the Raman scattering at each micro- or nano-rod of the 2D array is performed serially as groups of micro-rods or nano-rods resonate.

18. The sensing method as defined in claim 10 wherein each of the micro-rods or nano-rods includes a label for producing a distinct Raman signal.

19. The sensing method as defined in claim 18 wherein the label comprises: a Raman dye; a molecule or compound for selectively binding to an analyte of interest; or combinations thereof.

20. The sensing method as defined in claim 10 wherein each of the micro-rods or nano-rods includes a label, the label of each micro- or nano-rod in a single column being substantially the same, with the micro- or nano-rod label of each column being different from the micro- or nano-rod label of each other column, such that each column is for producing a different distinct Raman signal.

* * * * *